United States Patent

Halcom et al.

Patent Number: 6,156,927
Date of Patent: Dec. 5, 2000

[54] SUPPRESSION OF AGING FOR PD-AU VINYL ACETATE MONOMER CATALYST

[75] Inventors: Donald B. Halcom, Erie; Ronald L. Jagta, Waterford, both of Pa.

[73] Assignee: Engelhard Corporation, Iselin, N.J.

[21] Appl. No.: 09/245,599

[22] Filed: Feb. 5, 1999

Related U.S. Application Data

[60] Provisional application No. 60/073,837, Feb. 5, 1998.

[51] Int. Cl.⁷ ................................................. C07C 67/05
[52] U.S. Cl. ............................................................ 560/245
[58] Field of Search ............................... 560/245; 502/51, 502/55; 562/548, 607

[56] References Cited

U.S. PATENT DOCUMENTS

| | | | |
|---|---|---|---|
| 3,637,818 | 1/1972 | Krekeler et al. | |
| 4,087,622 | 5/1978 | Nakamura et al. | 560/245 |
| 4,158,737 | 6/1979 | Bartsch | 560/245 |
| 4,188,490 | 2/1980 | Hinnencamp et al. | 560/245 |
| 4,902,823 | 2/1990 | Wunder et al. | 560/245 |
| 5,700,753 | 12/1997 | Wang et al. | 502/330 |

FOREIGN PATENT DOCUMENTS 46-28523  8/1971  Japan .

OTHER PUBLICATIONS

International Search Report mailed Jul. 1, 1999 for PCT Patent Application Serial No. PCT/US99/02587.

Primary Examiner—James O. Wilson
Assistant Examiner—Robert W. Deemie
Attorney, Agent, or Firm—Raymond F. Keller

[57] ABSTRACT

One aspect of the present invention relates to a method of making vinyl acetate monomer, involving contacting reactant gases with a catalyst containing palladium, gold and a support in the presence of clean steam, the clean steam present from about 2 to about 10 psia, with the proviso that the support does not contain alumina or zinc oxide and the support is not treated with a sulfur containing compound. For example, the method of making vinyl acetate monomer may involve the reaction scheme:

$$O_2 + H_2O + CH_2CH_2 + CH_3CO_2H \rightarrow CH_3CO_2CH = CH_2 + H_2O.$$

Another aspect of the present invention relates to a method of regenerating a palladium-gold catalyst having an alumina-silica support during a process for making vinyl acetate monomer, with the proviso that the support does not contain alumina or zinc oxide and the support is not treated with a sulfur containing compound, involving temporarily stopping the process for making vinyl acetate monomer; contacting a gas mixture containing at least oxygen with the palladium-gold catalyst in the presence of clean steam at a temperature from about 100° C. to about 180° C., the clean steam present from at least about 2 psia and the oxygen present from at least about 2 psia; and restarting the process for making vinyl acetate monomer.

18 Claims, No Drawings

SUPPRESSION OF AGING FOR PD-AU VINYL ACETATE MONOMER CATALYST

This application claims the benefit of Provisional application No. 60/073,837, filed Feb. 5, 1998.

TECHNICAL FIELD

This invention generally relates to increasing the useful life of palladium-gold catalysts and to improved methods of making vinyl acetate monomer.

BACKGROUND OF THE INVENTION

Vinyl acetate monomer (VAM) is commercially produced predominately from the reaction of oxidatively coupling acetic acid with ethylene to form vinyl acetate plus water plus the waste product carbon dioxide. Traces of ethyl acetate, acetaldehyde, and further acetoxylation products are also formed. This reaction is conducted in the presence of a catalyst in a reactor containing many tubes that are typically about three centimeters in internal diameter and about six meters long. The shell side temperature of the reactor may be from about 100° C. to about 180° C. and the reaction pressure from about 35 psig (pounds per square inch gauge) to about 130 psig. The gas hourly space velocity (standard volumes of feed gas per volume of catalyst per hour) ranges from about 500 to about 4000 $hr^{-1}$.

Commercial experience reveals that the catalyst performance decreases with respect to time; that is, the catalyst undesirably ages. In particular, carbonaceous material may form on Pd—Au VAM catalysts during their use in commercial reactors. This formation is deleterious to the subsequent performance of these catalysts.

It is believed that this aging occurs by two mechanisms. The first mechanism for aging is essentially global for the entire catalyst charge in a reaction tube and is a sintering mechanism. The sintering mechanism is produced when the active catalytic component for the reaction (in this case palladium) undergoes a metallic rearrangement with respect to time such that the amount of catalyst available for reaction at the surface formed between the catalyst metal and the reactants decreases.

The second aging mechanism results from the deposition of a component that fouls the surface of the catalyst. Fouling of the catalyst surface blocks the surface to reactant access and thus decreases the reaction rate. This catalyst fouling usually begins at the reactor inlet, and with time progresses through the reactor tube until the surface is blocked to an extent where the catalyst becomes essentially useless.

SUMMARY OF THE INVENTION

In one embodiment, the present invention relates to a method of making vinyl acetate monomer, involving contacting reactant gases with a catalyst comprising palladium, gold and a support in the presence of clean steam, wherein the clean steam is present from about 2 to about 10 psia, with the proviso that the support does not comprise alumina or zinc oxide.

In another embodiment, the present invention relates to a method of regenerating a palladium-gold catalyst having an alumina-silica support during a process for making vinyl acetate monomer, involving temporarily stopping the process for making vinyl acetate monomer; contacting a gas mixture comprising at least oxygen with the palladium-gold catalyst in the presence of clean steam at a temperature from about 100° C. to about 180° C., wherein the clean steam is present from at least about 2 psia and the oxygen is present from at least about 2 psia; and restarting the process for making vinyl acetate monomer.

In yet another embodiment, the present invention relates to method of minimizing build-up of a carbonaceous material on a catalyst comprising palladium; gold and an alumina-silica support during a catalytic process, involving contacting reactants of the catalytic process with the catalyst in the presence of clean steam.

The present invention addresses fouling problems associated with Pd—Au catalysts, especially VAM catalysts, by suppressing the formation of the fouling agent. As a result of the present invention, Pd—Au catalysts can be used for longer periods of time and more efficiently compared to catalytic processes which do not employ clean steam with reactants.

DETAILED DESCRIPTION OF THE INVENTION

The present invention involves mixing clean steam with the reactant gas or gases entering a commercial reactor that results in a gaseous reaction mixture at reaction conditions containing the equivalent of about 2 to about 10 absolute pounds per square inch of steam pressure at the gas inlet to the reactor tubes. In a preferred embodiment, the present invention involves mixing clean steam with the reactant gases entering a commercial VAM (vinyl acetate monomer) reactor so that the gaseous reaction mixture contains, for example, the equivalent of about 2 to about 10 absolute pounds per square inch of steam pressure. The steam absolute pressure increases above the stated values as the reaction to form an end product such VAM proceeds through the reactor tubes due to the formation of more water. While not wishing to be bound by any theory, it is believed that the presence of steam from the inlet to the outlet of the reaction tubes suppresses the formation of harmful carbonaceous material and is useful for prolonging the performance of the catalyst over time. In one embodiment, the present invention applies specifically to a catalyst constituted by Pd—Au on a commercial KA-160 (Sud Chemie) support.

In some embodiments of the present invention, the clean steam is mixed with oxygen and removes carbonaceous material formed on a catalyst thereby regenerating the catalyst in situ. "In situ" is defined here to mean that the catalyst is not removed from the reactor used for the same purpose as the production of vinyl acetate monomer prior to the regeneration process. The operation of the catalyst may be continued for the purpose of producing more VAM product, or any other desired product, after the regeneration in the same reactor. The steam pressure is preferably at least about 2.0 psia and the oxygen pressure at least about 2.0 psia for the regeneration process. In one embodiment, the mixture of gases introduced into the reactor for regeneration contains from about 5% to about 25% oxygen and at least about 2.0 psia water.

In other words, regenerating the catalyst in situ involves stopping a catalytic process, typically temporarily, and mixing clean steam and oxygen at the gas inlet to the reactor tubes. Other inert gases, such as nitrogen, may also be present. Thus, clean steam may be mixed with air at the gas inlet to the reactor tubes. The carbonaceous material is removed or "burned off" of the catalyst. Subsequently, the catalytic process may be started again. The time consuming and burdensome proposition of removing reactor tubes and/or catalyst for cleaning is avoided. Catalytic processes may be carried out in a more efficient manner.

The amount of carbonaceous material formed on a catalyst is often measured by percent "coking". "Coking" is defined here as the formation of a carbonaceous material upon a catalyst that is characterized by a TGA analysis in air whereby the carbonaceous material is removed over a temperature range of about 250° C. to about 600° C.

Clean steam means pure water vapor or substantially pure water vapor. While clean steam may contain trace amounts of contaminants especially relatively inert contaminants (inert with respect to the catalytic reaction), clean steam does not contain significant amounts of contaminants that interfere with the catalytic reaction. In one embodiment, substantially pure water vapor contains about 99.5% or more water. In another embodiment, substantially pure water vapor contains about 99.9% or more water.

In one embodiment, an equivalent of about 2 to about 10 absolute pounds per square inch of steam pressure is contacted with the gaseous reaction mixture at the gas inlet to the reactor tubes. In another embodiment, an equivalent of about 3 to about 9 absolute pounds per square inch of steam pressure is contacted with the gaseous reaction mixture at the gas inlet to the reactor tubes. Alternatively, in one embodiment, after the reactant gas or gases are contacted with the clean steam to form the feed gas, the feed gas contains from about 1 mole % to about 8 mole % of clean steam. In another embodiment, the feed gas contains from about 1.5 mole % to about 7 mole % of clean steam. In yet another embodiment, the feed gas contains from about 2 mole % to about 6 mole % of clean steam.

In one embodiment, the temperature of the clean steam is from about 100° C. to about 180° C. In another embodiment, the temperature of the clean steam is from about 110° C. to less than about 170° C. In another embodiment, the temperature of the clean steam is from about 125° C. to about 150° C. Although clean steam may be intermittently contacted with reactant gases, it is preferable to continuously introduce clean steam into the feed gas as the catalytic proceeds.

The catalysts on which fouling agent formation is suppressed as a result of the present invention contain palladium, gold and a support. The catalysts thus include VAM catalysts among others. Other catalysts include allyl acetate catalysts, acetic acid catalysts and acetaldehyde catalysts. The ratio of gold to palladium is any ratio that permits the gold-palladium combination to function as a catalyst. In one embodiment, ratio (by weight) of gold to palladium in the catalyst is from about 0.1:1 to about 1.5:1. In another embodiment, ratio (by weight) of gold to palladium in the catalyst is from about 0.25:1 to about 1:1.

The catalyst support may be any material capable of supporting the gold-palladium combination. Examples of catalyst supports include alumina-silica, silica, carbon based supports, titania, zirconia, glass beads, diatomaceous earth, and the like. Alumina-silica supports are preferred. However, in one embodiment, the catalyst support does not contain zinc oxide. In another embodiment, the catalyst support does not contain alumina. In yet another embodiment, the catalyst support does not contain silica. In this connection, alumina supports and silica supports are different from each other and different from alumina-silica supports. In another embodiment, the catalyst support is not treated with a sulfur modifier, such as sulfur dioxide, sulfur trioxide, sulfuric acid, sulfurous acid, metal sulfates and other sulfur containing species.

Methods of making VAM using a palladium-gold catalyst are known. For example, reactant gases, such as acetic acid, ethylene and oxygen, in the vapor phase are contacted with a palladium-gold catalyst in a reactor. Contact may be made in any suitable manner including fixed bed, moving bed, or fluidized bed operations. Vinyl acetate monomer, sometimes along with by-products and/or side reactants, is collected, and then optionally concentrated and purified. Any suitable VAM synthetic methods using a catalyst containing palladium and gold may be employed in accordance with the present invention.

In one embodiment, the present invention relates to injecting water vapor with a feed gas normally containing only ethylene, acetic acid, oxygen and inert components then the rate of formation of a fouling agent may be dramatically decreased. The amount of water vapor that used is equal to or greater than the equivalent of two pounds per square inch absolute pressure at the reactor inlet. Extra water is formed during the catalytic reaction which increases further the absolute pressure of the water component through the reaction tube. The inlet addition of the water prevents the initial formation of the fouling agent at the reactor inlet which in turn the prevents the progressive build-up of fouling agent through the tube with respect to time. The injection of this minimum of water in the feed gas is preferably continued throughout the use of the catalyst.

The catalysts tested hereinbelow are commercially available catalysts produced by the Calsicat Division of Mallinckrodt Inc. The catalysts are prepared by substantially the same method except for metal content, and in some instances, the potassium acetate content. These catalyst are shell impregnated catalysts with the palladium and gold metals residing in a peripheral shell of about 500 microns in a sphere of about 5.2 millimeters diameter. The support for these catalysts is one supplied by Süd Chemie of Germany and is designated by them as KA -160. Its origin is from an acid leached clay and it is an alumina-silica based support. The catalyst tested have a ratio of Au:Pd (by weight) of about 0.45. In this specification, only the palladium content is specified in grams of palladium per liter of catalyst (the amount of gold may be determined based on the amount of palladium). The potassium acetate content of the catalyst is between about 30 and about 40 grams of potassium acetate per liter of catalyst.

The fouling agent deposited upon the VAM catalyst is characterized and quantified by using thermal gravimetric analysis (TGA). A DuPont 2100 TGA-DSC analyzer is used (in TGA mode) to determine the amount of fouling agent burned off in air from 250° C. to 600° C. when linearly programmed at 20° C. per minute. The burn off loss is computed by dividing the grams of weight loss between 250° C. to 600° C. per 100 gram is of final catalyst weight at 600° C. and reported this number as a percent loss (the loss based upon the final weight not starting weight). Corrections are made to these determinations by subtracting the same measured weight obtained from the starting virgin catalyst from that observed for the fouled catalyst. Using this method, results are obtained ranging from a few tenths of a percent to values as high as about 14% (obtained from a commercial spent catalyst). For shorthand purposes, the catalyst is described herein as having "x% Coke". The characteristic shape of the curve from the TGA analyses of fouled samples is the same for all of the determinations.

The appearance of the fouled catalyst changes with the degree of fouling. A virgin catalyst is gray externally while on the interior it is pure white (inside of the exterior metal shell). As the amount of fouling increases, the entire catalyst (including the white interior where no metal is present) turns tan at about 2–3% by weight fouling material to dark brown by about 6–8% fouling material. This discoloration throughout the catalyst pellet volume strongly indicates that the fouling mechanism is somehow homogeneous in nature. The darkest brown appearing pellets are almost always at the feed end of a reactor tube and the pellets are much lighter to "virgin" in appearance proceeding through the tube. The percentage by weight of the fouling typically decreases from the feed end to the exit end.

A laboratory reactor is constructed to measure the kinetics for the sintering and fouling of a catalyst. A quartz glass tube about 100 cm in length with an inside diameter of about 6 mm is jacketed with a Pyrex glass tube of about 3 cm diameter. Hot oil is pumped at a high velocity through the Pyrex glass jacket that surrounds the quartz tube. Broken quartz pieces are used to fill the bottom of the 6 mm quartz tube and then exactly fifty pellets of about 5.2 mm diameter are stacked (like a string of beads) in the 6 mm tube. On top of this, approximately 25 cm section of catalyst is added as an additional zone of broken quartz. Feed gas and acetic acid are metered into the top of the quartz tube using a metering pump and mass flow controllers and hot reaction products are withdrawn from the bottom and analyzed as a function of time on stream. The reactor is operated in an almost differential mode (low conversion of oxygen). Steady state is essentially present at all times. The reactor is essentially isothermal over the catalyst bed length and across the 6 mm diameter due to the high flow of hot oil in the jacket. Lauda K6 recirculating baths are used to supply the hot oil and maintain isothermal conditions with respect to time and geometry. The glacial acetic acid used for a reactor run is always distilled before use.

The top zone of broken quartz acts as a preheater which brings the reactants to the operating temperature. The liquid acetic acid fed to the quartz top zone is also vaporized. When water is used in a reactor run, it is fed by mixing doubly deionized water with the previously distilled glacial acetic acid. This reactor is typically operated at 120 psig (pounds per square inch gauge) inlet pressure with a total flow of gas to the reactor including the vaporized acetic acid of about 10.7 to 11.1 gm-moles of gas per hour. The computed volume of the fifty catalyst pellets is 6.8 cubic centimeters. This represents about a 35,000 hr$^{-1}$ gas space velocity (standard volumes of gas per volume of catalyst per hour). The feed gas composition is over the following range:

| Component | Amount |
|---|---|
| Ethylene | 79–82 mole percent |
| Acetic Acid | 8.5–10 mole percent |
| Oxygen | 4–8 mole percent |
| Water | 0–5 mole percent |

There are several reasons why the quartz reactor is operated at about the 35,000 hr$^{-1}$ space velocity. One reason is to have the reaction run under near or fully turbulent gas flow conditions. Actual full scale plant reactors are run at these conditions. Experience dictates that running laboratory reactors of this scale at the same space velocities as plant reactors means that the laboratory size reactor operates with the gas phase under essentially laminar flow conditions. This produces results which are incapable of scale up to plant conditions. The boundary layer around the catalyst pellets with laminar flow causes the reaction to become oxygen starved because the rate limiting step becomes the diffusion of oxygen across this boundary layer. The linear gas velocity in this 6 mm diameter reactor is about the same as the linear gas velocity in a full scale reactor. The reaction rate kinetics for the VAM reaction are fast enough to produce this problem.

Another reason for this type of reactor is to isolate and focus upon the environment that actual pellets experience at the inlet of commercial reactor tubes. The total volume of gas per unit time per catalyst pellet is about the same and the gas phase compositions are about the same at the inlets of both scale reactors.

Yet another reason is to obtain a differential reactor with low conversions in order to make the mathematics of performance analysis easier. Still yet another reason is to observe what happens during the duration of a catalyst run. This proves to be very useful.

The hot effluent gas from the reactor is analyzed with a Hewlett-Packard 5880A gas chromatography unit equipped with a HeyeSep-Q column. Results are obtained with the chromatography unit connected on-line to the reactor. After each analysis, the STY (space time yield) is computed. This is defined as the grams of VAM produced per liter of catalyst per hour.

After a run is complete, the amount of fouling agent near the inlet and exit of the fifty pellet reaction zone is measured using TGA. The inlet always contains more fouling agent than the exit and the inlet value is the value reported in this specification. The exit values for fouling are about 50% to about 75% of the values obtained at the inlet.

Analysis of the data in this specification shows that with near differential conversion:

1) the space time yield (STY) for VAM is directly proportional to the grams per liter of palladium in these catalysts. This means that the grams of VAM formed per unit time per gram of Pd present is essentially a constant at time equal to zero. This is at a given temperature, inlet gas composition and inlet pressure.

2) to a first approximation the STY is proportional to the square root of the absolute pressure of oxygen in the inlet gas. The absolute pressure of the oxygen does not substantially change through the reactor due to low conversion and is virtually a constant.

3) the apparent activation energy for the formation of VAM is about 8.0 Kcal per g-mole.

In view of these dependencies, one may define a special output variable. The Normalized Output Variable is defined as:

$$N=STY/(g/lPd*SQRT(psiaO_2)*1.274E6)*EXP(8000/(RT))$$

$$R=1.987 \text{ cal/g-mole}$$

The normalized output variable is temperature, metal loading and oxygen independent. This independence only applies to the STY effects. With this normalization, the values for "N" are 1.0 at time equal to zero and then decrease with time. The STY is the measured value at any time during the catalytic testing under constant inlet conditions. The net result is to multiply the observed value of the STY by a "constant" at specified test conditions.

One assumption is made. The assumption is that STY is directly proportional to the exposed area of catalyst present at any time. This assumption is made since the STY is directly proportional to the catalyst metal loading. Two simultaneous and independent catalyst decay mechanisms may be fit to the normalized values for "N".

The first decay mechanism is a classic second order sintering mechanism which in dimensionless integrated form looks like:

$$\text{Sintering}=1/(1+A*t) \text{ (This form fits best only over the range of this study.)}$$

The second decay mechanism is for linear fouling which in dimensionless integrated form looks like:

$$\text{Fouling}=B*t*EXP(-psiaH_2O)$$

In both of these decay equations "t" is the time. "A" and "B" are constants which have the units of reciprocal time. The exponential function in the fouling equation empirically explains the water dependence upon fouling. A factor could have multiplied the value of "psiaH$_2$O" but with these units, the factor appears to be about unity.

Combining all of the equations and all of the data from the experiments reported in this specification semi-empirically fit:

$N = 1/(1+A*t) - B*t*EXP(-psiaH_2O)$ $A = 0.126$ days$^{-1}$ $B = 0.0324$ days$^{-1}$ (both "A" and "B" are temperature independent)

The results from the time testing of various samples with different and in some cases repeat conditions are presented in tabular form from spreadsheets. Inlet conditions for each individual test are given along with a run number designation.

The following examples illustrate the present invention. Unless otherwise indicated in the following examples, in the specification and in the appended claims, all parts and percentages are by weight, temperatures are in degrees centigrade and pressures are at or near 120 psig.

EXAMPLE 1

| DAYS | Run SC424 STY | Temp° C. 160 STY/g/lPd | g/l Pd 10 N | psiaO$_2$ 10.8 1/(1 + A*t) | psiaH$_2$O 0 B*t*EXP(-C*psiaH2O) | %Coke 1.85 |
|---|---|---|---|---|---|---|
| 1 | 3196 | 319.6 | 0.8336 | 0.8881 | 0.0324 | |
| 2 | 3009 | 300.9 | 0.7848 | 0.7987 | 0.0648 | |
| 3 | 2673 | 267.3 | 0.6971 | 0.7257 | 0.0972 | |
| 4 | 2365 | 236.5 | 0.6168 | 0.6649 | 0.1296 | |
| 5 | 2100 | 210.0 | 0.5477 | 0.6135 | 0.1620 | |
| 6 | 1760 | 176.0 | 0.4590 | 0.5695 | 0.1944 | |

EXAMPLE 2

| DAYS | Run SR425 STY | Temp° C. 160 STY/g/lPd | g/l Pd 6 N | psiaO$_2$ 10.8 1/(1 + A*t) | psiaH$_2$O 0 B*t*EXP(-C*psiaH2O) | %Coke 2.94 |
|---|---|---|---|---|---|---|
| 1 | 1965 | 327.5 | 0.8542 | 0.8881 | 0.0324 | |
| 2 | 1569 | 261.5 | 0.6820 | 0.7987 | 0.0648 | |
| 3 | 1331 | 221.8 | 0.5786 | 0.7257 | 0.0972 | |
| 4 | 1096 | 182.7 | 0.4764 | 0.6649 | 0.1296 | |
| 5 | 918 | 153.0 | 0.3990 | 0.6135 | 0.1620 | |
| 6 | 763 | 127.2 | 0.3317 | 0.5695 | 0.1944 | |

EXAMPLE 3

| DAYS | Run SC426 STY | Temp° C. 140 STY/g/lPd | g/l Pd 10 N | psiaO$_2$ 10.8 1/(1 + A*t) | psiaH$_2$O 0 B*t*EXP(-C*psiaH2O) | %Coke 3.32 |
|---|---|---|---|---|---|---|
| 1 | 2076 | 207.6 | 0.8494 | 0.8881 | 0.0324 | |
| 2 | 1767 | 176.7 | 0.7230 | 0.7987 | 0.0648 | |
| 3 | 1520 | 152.0 | 0.6219 | 0.7257 | 0.0972 | |
| 4 | 1282 | 128.2 | 0.5245 | 0.6649 | 0.1296 | |
| 5 | 1036 | 103.6 | 0.4239 | 0.6135 | 0.1620 | |
| 6 | 815 | 81.5 | 0.3335 | 0.5695 | 0.1944 | |

EXAMPLE 4

| DAYS | Run SR427 STY | Temp° C. 140 STY/g/lPd | g/l Pd 6 N | psiaO$_2$ 10.8 1/(1 + A*t) | psiaH$_2$O 0 B*t*EXP(−C*psiaH2O) | %Coke 1.59 |
|---|---|---|---|---|---|---|
| 1 | 1111 | 185.2 | 0.7576 | 0.8881 | 0.0324 | |
| 2 | 988 | 164.7 | 0.6737 | 0.7987 | 0.0648 | |
| 3 | 912 | 152.0 | 0.6219 | 0.7257 | 0.0972 | |
| 4 | 794 | 132.3 | 0.5414 | 0.6649 | 0.1296 | |
| 5 | 699 | 116.5 | 0.4767 | 0.6135 | 0.1620 | |
| 6 | 624 | 104.0 | 0.4255 | 0.5695 | 0.1944 | |

EXAMPLE 5

| DAYS | Run SC428 STY | Temp° C. 140 STY/g/lPd | g/l Pd 10 N | psiaO$_2$ 10.6 1/(1 + A*t) | psiaH$_2$O 2.2 B*t*EXP(−C*psiaH2O) | %Coke 1.68 |
|---|---|---|---|---|---|---|
| 1 | 2102 | 210.2 | 0.8681 | 0.8881 | 0.0036 | |
| 2 | 1918 | 191.8 | 0.7921 | 0.7987 | 0.0072 | |
| 3 | 1680 | 168.0 | 0.6938 | 0.7257 | 0.0108 | |
| 4 | 1530 | 153.0 | 0.6319 | 0.6649 | 0.0144 | |
| 5 | 1360 | 136.0 | 0.5617 | 0.6135 | 0.0180 | |
| 6 | 1208 | 120.8 | 0.4989 | 0.5695 | 0.0215 | |

EXAMPLE 6

| DAYS | Run SR429 STY | Temp° C. 140 STY/g/lPd | g/l Pd 6 N | psiaO$_2$ 10.6 1/(1 + A*t) | psiaH$_2$O 2.2 B*t*EXP(−C*psiaH2O) | %Coke 0.43 |
|---|---|---|---|---|---|---|
| 1 | 1217 | 202.8 | 0.8377 | 0.8881 | 0.0036 | |
| 2 | 1118 | 186.3 | 0.7695 | 0.7987 | 0.0072 | |
| 3 | 994 | 165.7 | 0.6842 | 0.7257 | 0.0108 | |
| 4 | 942 | 157.0 | 0.6484 | 0.6649 | 0.0144 | |
| 5 | 850 | 141.7 | 0.5851 | 0.6135 | 0.0180 | |
| 6 | 818 | 136.3 | 0.5630 | 0.5695 | 0.0215 | |

EXAMPLE 7

| DAYS | Run SC432 STY | Temp° C. 140 STY/g/lPd | g/l Pd 10 N | psiaO$_2$ 10.5 1/(1 + A*t) | psiaH$_2$O 4.4 B*t*EXP(−C*psiaH2O) | %Coke 1.07 |
|---|---|---|---|---|---|---|
| 1 | 2095 | 209.5 | 0.8693 | 0.8881 | 0.0004 | |
| 2 | 1822 | 182.2 | 0.7560 | 0.7987 | 0.0008 | |
| 3 | 1660 | 166.0 | 0.6888 | 0.7257 | 0.0012 | |
| 4 | 1572 | 157.2 | 0.6523 | 0.6649 | 0.0016 | |
| 5 | 1432 | 143.2 | 0.5942 | 0.6135 | 0.0020 | |
| 6 | 1339 | 133.9 | 0.5556 | 0.5695 | 0.0024 | |

EXAMPLE 8

| DAYS | Run SR433 STY | Temp° C. 140 STY/g/lPd | g/l Pd 6 N | psiaO$_2$ 10.5 1/(1 + A*t) | psiaH$_2$O 4.4 B*t*EXP(−C*psiaH2O) | %Coke 0.51 |
|---|---|---|---|---|---|---|
| 1 | 1225 | 204.2 | 0.8472 | 0.8881 | 0.0004 | |
| 2 | 1114 | 185.7 | 0.7704 | 0.7987 | 0.0008 | |
| 3 | 1016 | 169.3 | 0.7027 | 0.7257 | 0.0012 | |
| 4 | 927 | 154.5 | 0.6411 | 0.6649 | 0.0016 | |
| 5 | 894 | 149.0 | 0.6183 | 0.6135 | 0.0020 | |
| 6 | 855 | 142.5 | 0.5913 | 0.5695 | 0.0024 | |

EXAMPLE 9

| DAYS | Run SR434 STY | Temp° C. 140 STY/g/lPd | g/l Pd 10 N | psiaO$_2$ 10.6 1/(1 + A*t) | psiaH$_2$O 4.4 B*t*EXP(−C*psiaH2O) | %Coke 2.59 |
|---|---|---|---|---|---|---|
| 1 | 2182 | 218.2 | 0.9011 | 0.8881 | 0.0004 | |
| 2 | 1989 | 198.9 | 0.8214 | 0.7987 | 0.0008 | |
| 3 | 1798 | 179.8 | 0.7426 | 0.7257 | 0.0012 | |
| 4 | 1628 | 162.8 | 0.6723 | 0.6649 | 0.0016 | |
| 5 | 1529 | 152.9 | 0.6315 | 0.6135 | 0.0020 | |
| 6 | 1410 | 141.0 | 0.5823 | 0.5695 | 0.0024 | |
| 7 | 1278 | 127.8 | 0.5278 | 0.5313 | 0.0028 | |
| 8 | 1152 | 115.2 | 0.4758 | 0.4980 | 0.0032 | |
| 9 | 1061 | 106.1 | 0.4382 | 0.4686 | 0.0036 | |
| 10 | 947 | 94.7 | 0.3911 | 0.4425 | 0.0040 | |
| 11 | 873 | 87.3 | 0.3605 | 0.4191 | 0.0044 | |
| 12 | 827 | 82.7 | 0.3415 | 0.3981 | 0.0048 | |

EXAMPLE 10

| DAYS | Run SR440 STY | Temp° C. 140 STY/g/lPd | g/l Pd 10 N | psiaO$_2$ 10.5 1/(1 + A*t) | psiaH$_2$O 4.3 B*t*EXP(−C*psiaH2O) | %Coke 0.99 |
|---|---|---|---|---|---|---|
| 1 | 2022 | 202.2 | 0.8390 | 0.8881 | 0.0004 | |
| 2 | 1847 | 184.7 | 0.7664 | 0.7987 | 0.0009 | |
| 3 | 1690 | 169.0 | 0.7013 | 0.7257 | 0.0013 | |
| 4 | 1531 | 153.1 | 0.6353 | 0.6649 | 0.0018 | |
| 5 | 1407 | 140.7 | 0.5838 | 0.6135 | 0.0022 | |
| 6 | 1275 | 127.5 | 0.5291 | 0.5695 | 0.0026 | |

EXAMPLE 11

| DAYS | Run SR443 STY | Temp° C. 140 STY/g/lPd | g/l Pd 10 N | psiaO$_2$ 5.3 1/(1 + A*t) | psiaH$_2$O 0 B*t*EXP(−C*psiaH2O) | %Coke 2.18 |
|---|---|---|---|---|---|---|
| 1 | 1286 | 128.6 | 0.7511 | 0.8881 | 0.0324 | |
| 2 | 1169 | 116.9 | 0.6828 | 0.7987 | 0.0648 | |
| 3 | 1063 | 106.3 | 0.6209 | 0.7257 | 0.0972 | |
| 4 | 926 | 92.6 | 0.5408 | 0.6649 | 0.1296 | |
| 5 | 818 | 81.8 | 0.4778 | 0.6135 | 0.1620 | |
| 6 | 735 | 73.5 | 0.4293 | 0.5695 | 0.1944 | |

EXAMPLE 12

| DAYS | Run SR444 STY | Temp° C. 140 STY/g/lPd | g/l Pd 10 N | psiaO$_2$ 5.1 1/(1 + A*t) | psiaH$_2$O 3.9 B*t*EXP(−C*psiaH2O) | %Coke 0.99 |
|---|---|---|---|---|---|---|
| 1 | 1390 | 139.0 | 0.8276 | 0.8881 | 0.0007 | |
| 2 | 1267 | 126.7 | 0.7544 | 0.7987 | 0.0013 | |
| 3 | 1179 | 117.9 | 0.7020 | 0.7257 | 0.0020 | |
| 4 | 1068 | 106.8 | 0.6359 | 0.6649 | 0.0026 | |
| 5 | 1033 | 103.3 | 0.6150 | 0.6135 | 0.0033 | |
| 6 | 959 | 95.9 | 0.5710 | 0.5695 | 0.0039 | |

EXAMPLE 13

| DAYS | Run SR448 STY | Temp° C. 140 STY/g/lPd | g/l Pd 10 N | psiaO$_2$ 10.5 1/(1 + A*t) | psiaH$_2$O 4.4 B*t*EXP(−C*psiaH2O) | %Coke 1.61 |
|---|---|---|---|---|---|---|
| 1 | 2176 | 217.6 | 0.9029 | 0.8881 | 0.0004 | |
| 2 | 1967 | 196.7 | 0.8162 | 0.7987 | 0.0008 | |
| 3 | 1815 | 181.5 | 0.7531 | 0.7257 | 0.0012 | |
| 4 | 1677 | 167.7 | 0.6959 | 0.6649 | 0.0016 | |
| 5 | 1499 | 149.9 | 0.6220 | 0.6135 | 0.0020 | |
| 6 | 1369 | 136.9 | 0.5681 | 0.5695 | 0.0024 | |
| 7 | 1285 | 128.5 | 0.5332 | 0.5313 | 0.0028 | |
| 8 | 1156 | 115.6 | 0.4797 | 0.4980 | 0.0032 | |
| 9 | 1053 | 105.3 | 0.4369 | 0.4686 | 0.0036 | |
| 10 | 964 | 96.4 | 0.4000 | 0.4425 | 0.0040 | |
| 11 | 906 | 90.6 | 0.3759 | 0.4191 | 0.0044 | |
| 12 | 807 | 80.7 | 0.3349 | 0.3981 | 0.0048 | |

EXAMPLE 14

| DAYS | Run SR451 STY | Temp° C. 140 STY/g/lPd | g/l Pd 10 N | psiaO$_2$ 5.4 1/(1 + A*t) | psiaH$_2$O 6.7 B*t*EXP(−C*psiaH2O) | %Coke 0.57 |
|---|---|---|---|---|---|---|
| 1 | 1584 | 158.4 | 0.9165 | 0.8881 | 0.0000 | |
| 2 | 1385 | 138.5 | 0.8014 | 0.7987 | 0.0001 | |
| 3 | 1304 | 130.4 | 0.7545 | 0.7257 | 0.0001 | |
| 4 | 1240 | 124.0 | 0.7175 | 0.6649 | 0.0002 | |
| 5 | 1143 | 114.3 | 0.6614 | 0.6135 | 0.0002 | |
| 6 | 1075 | 107.5 | 0.6220 | 0.5695 | 0.0002 | |

EXAMPLE 15

| DAYS | Run SR452 STY | Temp° C. 140 STY/g/lPd | g/l Pd 6 N | psiaO$_2$ 5.4 1/(1 + A*t) | psiaH$_2$O 6.7 B*t*EXP(−C*psiaH2O) | %Coke 0.15 |
|---|---|---|---|---|---|---|
| 1 | 882 | 147.0 | 0.8506 | 0.8881 | 0.0000 | |
| 2 | 838 | 139.7 | 0.8081 | 0.7987 | 0.0001 | |
| 3 | 795 | 132.5 | 0.7667 | 0.7257 | 0.0001 | |
| 4 | 753 | 125.5 | 0.7262 | 0.6649 | 0.0002 | |
| 5 | 714 | 119.0 | 0.6886 | 0.6135 | 0.0002 | |
| 6 | 673 | 112.2 | 0.6490 | 0.5695 | 0.0002 | |

EXAMPLE 16

| DAYS | Run SC453 STY | Temp° C. 160 STY/g/lPd | g/l Pd 10 N | psiaO$_2$ 5.44 1/(1 + A*t) | psiaH$_2$O 6.7 B*t*EXP(−C*psiaH2O) | %Coke 0.75 |
|---|---|---|---|---|---|---|
| 1 | 2094 | 209.4 | 0.7695 | 0.8881 | 0.0000 | |
| 2 | 1901 | 190.1 | 0.6986 | 0.7987 | 0.0001 | |
| 3 | 1783 | 178.3 | 0.6552 | 0.7257 | 0.0001 | |
| 4 | 1587 | 158.7 | 0.5832 | 0.6649 | 0.0002 | |
| 5 | 1472 | 147.2 | 0.5409 | 0.6135 | 0.0002 | |
| 6 | 1332 | 133.2 | 0.4895 | 0.5695 | 0.0002 | |

EXAMPLE 17

| DAYS | Run SR454 STY | Temp° C. 160 STY/g/lPd | g/l Pd 6 N | psiaO$_2$ 5.44 1/(1 + A*t) | psiaH$_2$O 6.7 B*t*EXP(−C*psiaH2O) | %Coke 0.24 |
|---|---|---|---|---|---|---|
| 1 | 1493 | 248.8 | 0.9144 | 0.8881 | 0.0000 | |
| 2 | 1367 | 227.8 | 0.8372 | 0.7987 | 0.0001 | |
| 3 | 1208 | 201.3 | 0.7399 | 0.7257 | 0.0001 | |
| 4 | 1096 | 182.7 | 0.6713 | 0.6649 | 0.0002 | |
| 5 | 981 | 163.5 | 0.6008 | 0.6135 | 0.0002 | |
| 6 | 937 | 156.2 | 0.5739 | 0.5695 | 0.0002 | |

EXAMPLE 18

| DAYS | Run SR462 STY | Temp° C. 140 STY/g/lPd | g/l Pd 3.9 N | psiaO$_2$ 10.8 1/(1 + A*t) | psiaH$_2$O 0 B*t*EXP(-C*psiaH2O) | %Coke 1.29 |
|---|---|---|---|---|---|---|
| 1 | 713 | 182.8 | 0.7480 | 0.8881 | 0.0324 | |
| 2 | 635 | 162.8 | 0.6662 | 0.7987 | 0.0648 | |
| 3 | 558 | 143.1 | 0.5854 | 0.7257 | 0.0972 | |
| 4 | 402 | 103.1 | 0.4217 | 0.6649 | 0.1296 | |
| 5 | 388 | 99.5 | 0.4070 | 0.6135 | 0.1620 | |
| 6 | 271 | 69.5 | 0.2843 | 0.5695 | 0.1944 | |

EXAMPLE 19

| DAYS | Run SR464 STY | Temp° C. 140 STY/g/lPd | g/l Pd 10 N | psiaO$_2$ 10.4 1/(1 + A*t) | psiaH$_2$O 6.2 B*t*EXP(-C*psiaH2O) | %Coke 1.22 |
|---|---|---|---|---|---|---|
| 1 | 2054 | 205.4 | 0.8564 | 0.8881 | 0.0001 | |
| 2 | 1917 | 191.7 | 0.7993 | 0.7987 | 0.0001 | |
| 3 | 1764 | 176.4 | 0.7355 | 0.7257 | 0.0002 | |
| 4 | 1624 | 162.4 | 0.6771 | 0.6649 | 0.0003 | |
| 5 | 1456 | 145.6 | 0.6071 | 0.6135 | 0.0003 | |
| 6 | 1379 | 137.9 | 0.5750 | 0.5695 | 0.0004 | |
| 7 | 1277 | 127.7 | 0.5324 | 0.5313 | 0.0005 | |
| 8 | 1165 | 116.5 | 0.4857 | 0.4980 | 0.0005 | |
| 9 | 1112 | 111.2 | 0.4636 | 0.4686 | 0.0006 | |
| 10 | 1070 | 107.0 | 0.4461 | 0.4425 | 0.0007 | |
| 11 | 1030 | 103.0 | 0.4294 | 0.4191 | 0.0007 | |
| 12 | 959 | 95.9 | 0.3998 | 0.3981 | 0.0008 | |

An experiment is performed which demonstrates an ability to recover a large portion of the activity by conducting an in situ burn off of the fouling agent. In this experiment, the catalyst is aged for eleven days with zero water in the feed gas. The catalyst in the quartz tube is treated overnight with about 3.78 g-moles per hour of a gas at 150° C. and 120 psig containing 29 mole percent water and 71 mole percent nitrogen. The catalytic performance is subsequently measured and no improvement in the performance found.

This ineffective treatment is followed by another overnight treatment. The second treatment involved using about 4.64 g-moles per hour of gas at 150° C. and 120 psig containing 24 mole percent water, 18 mole percent oxygen and 58 mole percent nitrogen. A subsequent performance test is then performed and a significant portion of the expected catalyst activity is recovered. These data are shown in Run SR461. The expected value for "N" at this point in the catalyst's life is about 0.37 and after regeneration a value of about 0.28 is obtained. This represents about 76% of the hoped for recovery value for the catalytic performance. This represented a significant catalytic improvement and demonstrated that indeed a carbonaceous residue is formed on the catalyst. During the burn off of the carbonaceous residue deposited over the catalytic surface, only nitrogen, water, oxygen and most importantly carbon dioxide are observed evolving from the catalyst by chromatographic analysis.

| DAYS | Run SR461 STY | Temp° C. 140 STY/g/lPd | g/l Pd 10 N | psiaO$_2$ 10.7 1/(1 + A*t) | psiaH$_2$O 0 B*t*EXP(-C*psiaH2O) | %Coke |
|---|---|---|---|---|---|---|
| 1 | 2018 | 201.8 | 0.8295 | 0.8881 | 0.0324 | |
| 2 | 1773 | 177.3 | 0.7288 | 0.7987 | 0.0648 | |
| 3 | 1553 | 155.3 | 0.6384 | 0.7257 | 0.0972 | |
| 4 | 1296 | 129.6 | 0.5327 | 0.6649 | 0.1296 | |
| 5 | 1075 | 107.5 | 0.4419 | 0.6135 | 0.1620 | |
| 6 | 871 | 87.1 | 0.3580 | 0.5695 | 0.1944 | |
| 7 | 660 | 66.0 | 0.2713 | 0.5313 | 0.2268 | |
| 8 | 438 | 43.8 | 0.1800 | 0.4980 | 0.2592 | |
| 9 | 304 | 30.4 | 0.1250 | 0.4686 | 0.2916 | |
| 10 | 262 | 26.2 | 0.1077 | 0.4425 | 0.3240 | |
| 11 | 203 | 20.3 | 0.0834 | 0.4191 | 0.3564 | |
| 14 | 681 | 68.1 | 0.2799 | 0.3618 | After Regeneration | 3.81 |

Another experiment is conducted to elucidate further the regeneration process for recovering catalytic performance via residue burn off. Similar to Run SR461, a run is conducted for twelve days with zero water in the feed gas to foul the catalyst with residue. This is followed with an overnight treatment using 3.51 g-moles per hour of gas at 120 psig and 150° C. containing 24 mole percent oxygen and 76 mole percent nitrogen. This is Run SR466.

This overnight treatment is followed with a performance test which resulted in the performance increasing from an "N" value of 0.0691 to a value of 0.1092. This is judged to be of marginal value. The value of "N" for sintering only is about 0.40 at this point in time.

Another overnight treatment is used in Run SR466 which involved using 4.62 g-moles per hour of gas containing 24 mole percent water vapor, 18 mole percent oxygen and 58 mole percent nitrogen at 120 psig and 120° C. This treatment is again followed by a performance test. The value for "N" is measured at 0.2835. This illustrates the beneficial effect of water vapor upon the residue burn off rate. With sintering only, the value of "N" is about 0.38 at this point in time.

The form for the regression is then:
Y=X1+X2
Where: Y=N:X1=Sintering Function:X2=Fouling Function.

If the assumed equations are perfect and if there are no errors in any of the analytical data, the values for "R Squared", the coefficient multiplying the sintering function and the coefficient multiplying the fouling function would all have values of exactly one. In normal statistical parlance, a value of "R Squared" of about 0.95 indicates that about 95% of the data is explained by the correlation. It is estimated that the analytical error is about five percent on this basis and the 5% figure obtained from this correlation is considered to be in reasonable agreement with the estimated experimental error. The factors multiplying the assumed functions also are close to the expected values of one.

Another additional experiment that is performed involved treating a sample that is a catalyst support only (Sud Chemie KA160) for twelve days with the normal quartz glass reactor

| DAYS | Run SR466 STY | Temp° C. 140 STY/g/lPd | g/l Pd 10 N | psiaO$_2$ 10.8 1/(1 + A*t) | psiaH$_2$O 0 B*t*EXP(−C*psiaH2O) | %Coke |
|---|---|---|---|---|---|---|
| 1 | 1915 | 191.5 | 0.7835 | 0.8881 | 0.0324 | |
| 2 | 1644 | 164.4 | 0.6726 | 0.7987 | 0.0648 | |
| 3 | 1413 | 141.3 | 0.5781 | 0.7257 | 0.0972 | |
| 4 | 1177 | 117.7 | 0.4816 | 0.6649 | 0.1296 | |
| 5 | 957 | 95.7 | 0.3916 | 0.6135 | 0.1620 | |
| 6 | 784 | 78.4 | 0.3208 | 0.5695 | 0.1944 | |
| 7 | 579 | 57.9 | 0.2369 | 0.5313 | 0.2268 | |
| 8 | 451 | 45.1 | 0.1845 | 0.4980 | 0.2592 | |
| 9 | 300 | 30.0 | 0.1227 | 0.4686 | 0.2916 | |
| 10 | 184 | 18.4 | 0.0753 | 0.4425 | 0.3240 | |
| 11 | 169 | 16.9 | 0.0691 | 0.4191 | 0.3564 | |
| 12 | 267 | 26.7 | 0.1092 | 0.3981 | After O$_2$ & N$_2$ | |
| 13 | 693 | 69.3 | 0.2835 | 0.3791 | After H$_2$O, O$_2$ & N$_2$ | 2.97 |

All of the appropriate data are analyzed with the multiple linear regression tool supplied with the Lotus 1-2-3 spreadsheet program to regress the assumed functions for sintering and fouling against the value "N". The fit found for the data is considered to be excellent.

Regression Output:

| Constant | 0 | |
|---|---|---|
| Std Err of Y Est | 0.0409 | |
| R Squared | 0.9540 | |
| No. of Observations | 154 | |
| Degrees of Freedom | 152 | |
| | 1/(1 + A*t) | B*t*EXP(−C*psiaH$_2$O) |
| X Coefficient(s) | 0.9799 | −1.0428 |
| Std Err of Coef. | 0.0055 | 0.0363 |

The Normalized Output Dependent Variable is Defined as:

$$N=STY/(g/lPd*SQRT(psiaO_2)* 1.274E6)*EXP(8000/(RT))$$

$A=0.126 \text{days}^{-1}$ $R=1.987$ cal/g-mole $B=0.0324$ days$^{-1}$ $C=1.000$ days$^{-1}$ $$N=1/(1+A*t)-B*t*EXP(-C*psiaH_2O)$$

feed gas that contained zero water content. The resulting support is analyzed and 1.88% Coke is found. This strongly indicates that the presence of the "coking" agent (or its precursor) is in the feed gas and that it deposits on almost any support.

While not wishing to be bound by any theory, it is believed that the beneficial effects of the present invention are due to the presence of water in the feed gas which promotes the continuous palladium catalyzed burn off of carbonaceous residue deposited upon the catalyst at the normal operating conditions for the VAM reaction.

While the invention has been explained in relation to its preferred embodiments, it is to and components be understood that various modifications thereof will become apparent to those skilled in the art upon reading the specification. Therefore, it is to be understood that the invention disclosed herein is intended to cover such modifications as fall within the scope of the appended claims.

What is claimed is:

1. A method of making vinyl acetate monomer, comprising: contacting reactant gases with a catalyst comprising palladium, gold and a support in the presence of clean steam, wherein the clean steam is present from about 2 to about 10 psia, with the proviso that the support does not comprise alumina or zinc oxide and the support is not treated with a sulfur containing compound.

2. A method according to claim 1, wherein the support comprises alumina-silica.

3. A method according to claim 1, wherein the reactant gases comprise acetic acid, ethylene and oxygen.

4. A method according to claim 1, wherein the catalyst comprises a ratio of gold to palladium from about 0.1:1 to about 1.5:1 (by weight).

5. A method according to claim 1, wherein the clean steam has a temperature from about 100° C. to about 180° C.

6. A method according to claim 1, wherein the clean steam comprises about 99.9% or more pure water.

7. A method of regenerating a palladium-gold catalyst having an alumina-silica support during a process for making vinyl acetate monomer, with the proviso that the support does not comprise alumina or zinc oxide and the support is not treated with a sulfur containing compound, comprising:

temporarily stopping the process for making vinyl acetate monomer;

contacting a gas mixture comprising at least oxygen with the palladium-gold catalyst in the presence of clean steam at a temperature from about 100° C. to about 180° C., wherein the clean steam is present from at least about 2 psia and the oxygen is present from at least about 2 psia; and restarting the process for making vinyl acetate monomer.

8. A method according to claim 7, wherein the clean steam is at a temperature from about 110° C. to less than about 170° C.

9. A method according to claim 7, wherein the gas mixture comprising oxygen further comprises nitrogen.

10. A method according to claim 7, wherein the clean steam comprises about 99.9% or more pure water.

11. A method of minimizing build-up of a carbonaceous material on a catalyst comprising palladium, gold and an alumina-silica support during a catalytic process, with the proviso that the support does not comprise alumina or zinc oxide, comprising:

contacting reactants of the catalytic process with the catalyst in the presence of clean steam.

12. A method according to claim 11, wherein the reactants comprise at least one of ethylene, oxygen and acetic acid.

13. A method according to claim 11, wherein the clean steam and the reactants constitute a feed gas, and the feed gas comprises from about 1 mole percent to about 8 mole percent water.

14. A method according to claim 11, wherein the clean steam and the reactants constitute a feed gas, and the feed gas comprises from about 1.5 mole percent to about 7 mole percent water.

15. A method according to claim 11, wherein the clean steam has a temperature from about 125° C. to about 150° C.

16. A method according to claim 11, wherein the catalytic process is a method of making vinyl acetate monomer.

17. A method according to claim 11, wherein the catalytic process is a method of making at least one of allyl acetate, acetic acid, and acetaldehyde.

18. A method according to claim 11, wherein the clean steam comprises about 99.5% or more pure water.

* * * * *